United States Patent [19]
Leschinsky

[11] Patent Number: 5,904,713
[45] Date of Patent: May 18, 1999

[54] INVERTIBLE BIFURCATED STENT/GRAFT AND METHOD OF DEPLOYMENT

[75] Inventor: Boris Leschinsky, Waldwick, N.J.

[73] Assignee: Datascope Investment Corp., Montvale, N.J.

[21] Appl. No.: 08/892,410

[22] Filed: Jul. 14, 1997

[51] Int. Cl.[6] .................................................. A61F 2/06
[52] U.S. Cl. .................................................. 623/1
[58] Field of Search .................................. 623/1, 11, 12

[56] References Cited

U.S. PATENT DOCUMENTS

| | | | |
|---|---|---|---|
| 5,609,625 | 3/1997 | Piplani | 623/1 |
| 5,628,783 | 5/1997 | Quiachon | 623/1 |
| 5,639,278 | 6/1997 | Dereume | 623/1 |
| 5,693,087 | 12/1997 | Parodi | 623/1 |
| 5,693,088 | 12/1997 | Lazarus | 623/1 |
| 5,755,770 | 5/1998 | Ravenscroft | 623/1 |
| 5,755,778 | 5/1998 | Kleshinski | 623/1 |

*Primary Examiner*—Michael J. Milano
*Attorney, Agent, or Firm*—J. Gary Mohr; Abraham P. Ronai

[57] ABSTRACT

A single-piece bifurcated graft for insertion into the femoral artery and further into the aorta with approximately one half of the graft inverted inside out after positioning within the artery. There is no central section like other bifurcated grafts. Instead, two bifurcated sections are joined at the top. Upon introduction, the graft is attached to the aortic wall in the middle section, the vicinity of the renal arteries, and the inversion process takes place. This process allows deployment of the second half of the graft into its final inverted position. While stents are located only at the openings of the graft, additional stents may be deployed inside the graft if necessary.

8 Claims, 2 Drawing Sheets

INVERTIBLE BIFURCATED STENT/GRAFT AND METHOD OF DEPLOYMENT

BACKGROUND OF THE INVENTION

1. Field of the Invention

The invention relates to a bilateral intra-aortic bypass graft for intraluminal delivery, and a method for deployment of the graft.

2. Description of the Prior Art

Grafts are used for treating of abdominal aortic aneurism. To avoid major surgery, procedures and devices have and are being developed to introduce these grafts and attach them to the aortic wall via a cut-down and insertion of the device through the femoral artery. Upon introduction, the device is expanded and affixed to the walls of the aorta. This femoral introduction and deployment of the graft is achieved, however, with great difficulties since one section of the graft has to be moved from one side of the patient to the other. One way that this was accomplished in the prior art was to use in general a graft having a main tubular body and first and second tubular legs joined to said main body in a bifurcation. The main body and the legs were formed of a flexible surgically implantable material. The main body and the first and second legs each had an opening therein in communication with the other openings. Expandable spring attachment means were secured to the main body adjacent the opening in the main body. Additional spring attachment means were secured to the first leg adjacent the opening in that leg. The major deployment device was a capsule catheter and a balloon catheter. The capsule catheter usually was a flexible elongate tubular member having proximal and distal extremities. A capsule was mounted on the distal extremity of the flexible elongate tubular member and had an open end. A graft is disposed within the capsule. The balloon catheter was a flexible elongate tubular member having proximal and distal extremities. A balloon was secured to the distal extremity of the flexible elongate tubular member of the balloon catheter. The flexible elongate tubular member of the balloon catheter extended through the graft and through the flexible capsule in which the graft was disposed and through the flexible elongated tubular member of the capsule catheter. Retention means were carried by the flexible elongate tubular member of the balloon catheter and to engage the graft. A control mechanism was provided that had a handle portion adapted to be grasped by a human hand. Means were further provided for securing the flexible elongate tubular member of the capsule catheter to the first part. The flexible elongate tubular member of the balloon catheter extended through the first part and through the control mechanism. Means carried by the control mechanism causes movement of the first part with respect to the second part to thereby cause the capsule to be withdrawn from over the graft and permitting the retention means to retain the graft in position so that it is ejected from the capsule as the first part is moved relative to the second part.

SUMMARY OF THE INVENTION

A method and device for deploying a graft having bifurcation with a main body and first and second legs is provided for deployment across the aortic bifurcation and into the first and second iliac arteries of a patient to repair an aneurysm therein comprising folding one of the legs of the graft so it lies substantially parallel to the main body of the graft, introducing the graft through the femoral artery until the distal portion of the graft is disposed proximal of the aortic aneurysm, securing the proximal extremity of the graft with the other leg of the graft being disposed in the first iliac artery, pulling down the folded over leg into the second iliac artery securing the distal extremity of the first leg of the graft in the first iliac artery and thereafter securing the second leg of the graft in the second iliac artery.

It is an object of this invention to provide a method and apparatus for the percutaneous treatment of aneurysms.

Another object of this invention is to provide a method and apparatus for treating aneurysms located at a vessel bifurcation.

A further object of this invention is to provide a simple device and method for treating aneurysms located at a vessel bifurcation that allows for positive position without the problems associated with joining multiple units of a graft.

BRIEF DESCRIPTION OF THE DRAWINGS

The appended claims particularly point out and distinctly claim the subject matter of this invention. The various objects, advantages and novel features of this invention will be more fully apparent from a rending of the following detailed description in conjunction with the accompanying drawings in which like reference numerals refer to like parts and in which:

DESCRIPTION OF ILLUSTRATIVE EMBODIMENTS OF THE INVENTION

Figure 1:
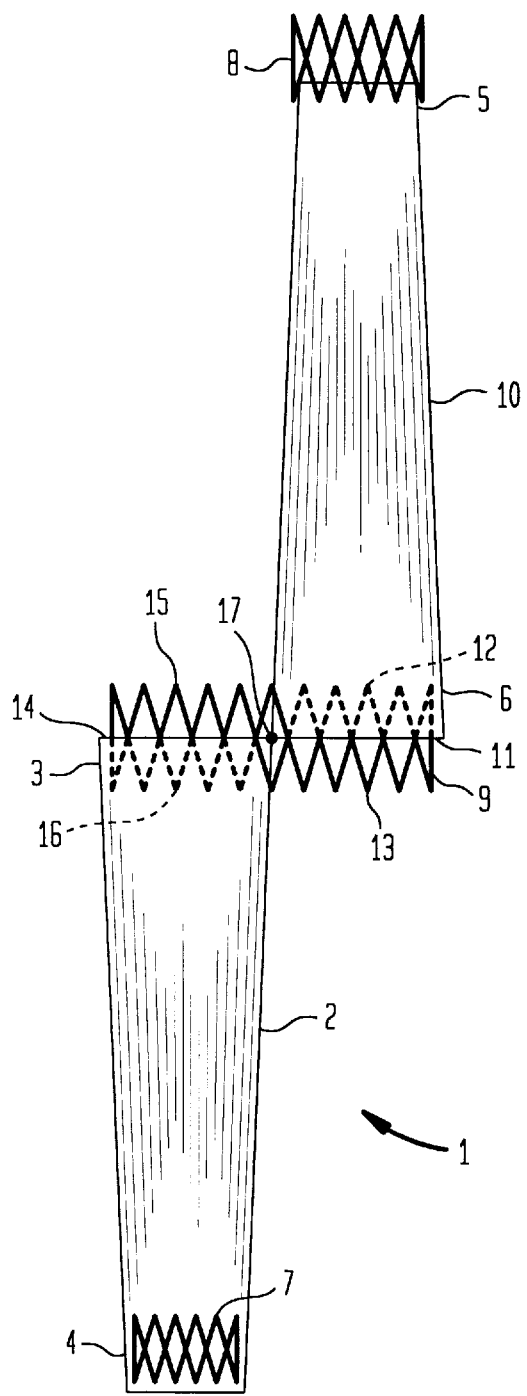
FIG. 1 is a front view of the expanded graft of the present invention showing both legs of the graft in a non-inverted state prior to wrapping for insertion into the femoral artery.
Figure 3:
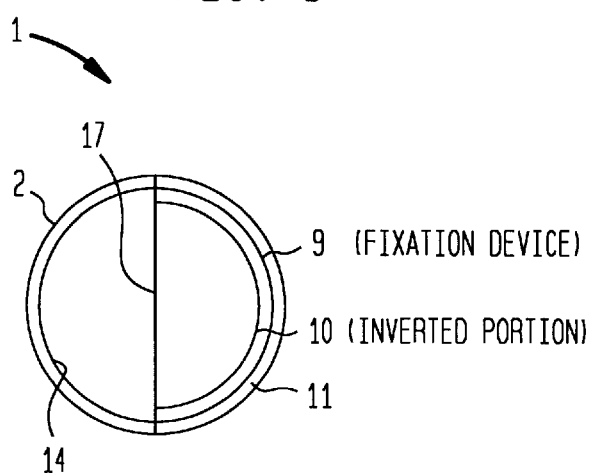
FIG. 3 is a top view of the expanded graft of the present invention showing the cross-section of the deployed graft of FIG. 2.

The invention relates to an endovascular graft prosthesis for arrangement at or in the vicinity of a bifurcation in the arterial system of a patient and comprising a substantially tubular top body for location in an upstream arteria above the bifurcation and substantially tubular legs extending from the top body extending via the bifurcation into each of two downstream branch arteries, said graft being made of a flexible microporous and surgically implantable woven material unpenetratable to blood.

In particular, the invention is concerned with the repair of an aneurysm in the vicinity of the aortic bifurcation, but it may also be applied to other parts of the arterial system where a principal unstream arteria bifurcates into two branch arteries.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

I claim:

1. A graft device comprising a first tubular leg and a second tubular leg each having a top end and a bottom end the top end, of the first leg and the bottom end of the second leg are partially connected along a septum, the first leg and the second leg are substantially parallel, the second leg is capable of inversion, upon deployment the second leg is inverted and the first leg and the second leg are substantially parallel and are side by side and the length of the graft device extends substantially from the septum to the bottom end of the first leg or substantially from the septum to the top of the second leg.

2. The graft device as claimed in claim 1 further comprising fixation means for fixing the top end and the bottom end of the first leg and the second leg within a vessel.

3. The graft device as claimed in claim 1 further comprising stents for fixing the top end and the bottom end of the first leg and the second leg within a vessel.

4. The graft device as claimed in claim 1 wherein the first leg and the second leg each have a D-shape cross sectional area comprising a flat portion and a curved portion and wherein the septum is flat, upon inversion of the second leg the first leg and the second leg together have a substantially round cross section and assume the cross sectional shape of the vessel.

5. The graft device as claimed in claim 1 wherein the first leg and the second leg each have a D-shape cross sectional area comprising a flat portion and a curved portion and wherein the septum is flat, upon inversion of the second leg the first leg and the second leg together have a substantially round cross section and assume the cross sectional shape of the vessel, and wherein the first leg and the second leg are tapered such that the cross sectional area of the bottom end of the first leg is smaller than that of the top end of the first leg and the cross sectional area of the top end of the second leg is smaller than that of the bottom end of the second leg.

6. A graft device for insertion into a bifurcated vessel comprising a first tubular leg and a second tubular leg each having a top end and a bottom end, and fixation devices for fixing the top end and the bottom end of the first leg and the second leg within the vessel, the top end of the first leg and the bottom end of the second leg are partially connected along a flat septum, the first leg and the second leg are substantially parallel and do not communicate, the second leg is capable of inversion, upon inversion of the second leg the first leg and the second leg are substantially parallel and are side by side, the first leg and the second leg each have a D-shape cross sectional area comprising a flat portion and a curved portion, upon inversion of the second leg the first leg and the second leg together have a substantially round cross section and assume the cross sectional shape of the vessel, the first leg and the second leg are tapered such that the cross sectional area of the bottom end of the first leg is smaller than that of the top end of the first leg and the cross sectional area of the top end of the second leg is smaller than that of the bottom end of the second leg.

7. A method for bridging a bifurcated aneurysm in a blood vessel with a graft device comprising a first tubular leg and a second tubular leg each having a top end and a bottom end, and fixation means for fixing the top end and the bottom end of the first leg and the second leg within the vessel, the top end of the first leg and the bottom end of the second leg are partially connected along a flat septum, the first leg and the second leg are substantially parallel, the second leg is capable of inversion, upon inversion of the second leg the first leg and the second leg are substantially parallel and are side by side and the length of the graft device extends substantially from the septum to the bottom end of the first leg or substantially from the septum to the top end of the second leg, comprising the steps of:

(a) percutaneously inserting the graft device into a first leg of the bifurcated blood vessel;

(b) deploying fixation means at the bottom end and the top end of the fist leg which is downstream of the second leg;

(c) inverting the second leg of the graft device;

(d) deploying the fixation means in the bottom end and the top end of the inverted second leg.

8. The method for bridging a bifurcated aneurysm in a blood vessel as claimed in claim 7 wherein the fixation means comprises stents.

* * * * *

UNITED STATES PATENT AND TRADEMARK OFFICE
CERTIFICATE OF CORRECTION

PATENT : 5,904,713

DATED : May 18, 1999

INVENTOR(S) : Boris Leschinsky

It is certified that error appears in the above-identified patent and that said Letters Patent is hereby corrected as shown below:

Column 3, line 1, after "top end" delete the comma.

Signed and Sealed this

Twenty-sixth Day of October, 1999

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT : 5,904,713

DATED : May 18, 1999

INVENTOR(S) : Boris Leschinsky

Figure 2:
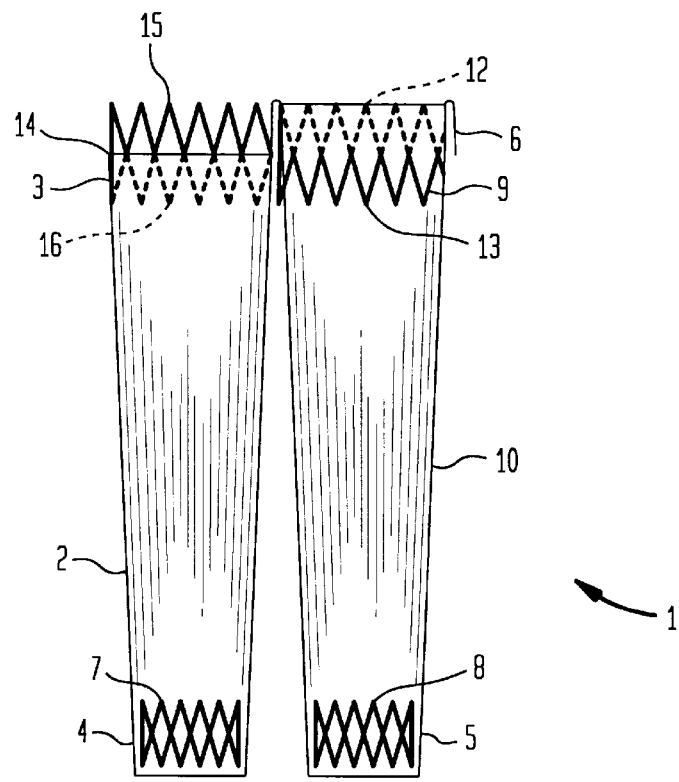
FIG. 2 is a front view of the expanded graft of the present invention showing both legs of the graft in the relationship they will have after deployment within the artery where one of the legs is inverted.
Figure 4:
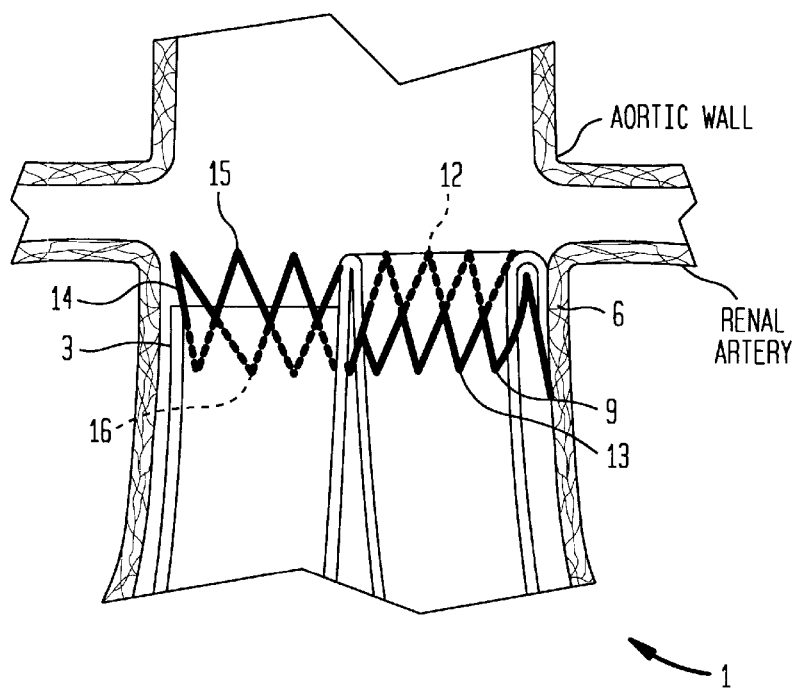
FIG. 4 is a side view of the deployed graft of FIG. 2 fixed to the internal portion of the artery just below the renal arteries.

It is certified that error appears in the above-identified patent and that said Letters Patent is hereby corrected as shown below:

Column 2, line 27, "non inverter" should read --non-inverter--.
Column 2, line 55, insert the following:

-- FIG. 1 illustrates a graft 1 comprising a first leg 2, having a top end 3 and a bottom end 4, second leg 10 is longer than first leg 2 so that upon inversion, as illustrated in FIG 2, the graft 1 has one uniform length. Note that the taper on the second leg 10 facilitates inversion of the second leg 10 by preventing the second leg 10 from buckling while the top end 5 of the second leg 10 is pulled through the second leg 10.

FIG. 2 illustrates the graft 1 with the second leg 10 in an inverted state. The bottom portion 13 of the right half 11 of the third fixation device 9 is now disposed about the second leg 10.

Since the above described graft 1 is one piece any and all the connection problems of the prior art devices have been eliminated. Furthermore, the fact that the fixation devices are deployed at different times allows for more accurate final placement of graft 1.

UNITED STATES PATENT AND TRADEMARK OFFICE
CERTIFICATE OF CORRECTION

PATENT NO. : 5,904,713
DATED : May 18, 1999
INVENTOR(S) : Boris Leschinsky

It is certified that error appears in the above-identified patent and that said Letters Patent is hereby corrected as shown below:

From the foregoing it can be seen that there has been provided a graft having a bifurcation in which the legs are firmly attached in the arterial vessels so that they cannot accidentally become dislodged from the location which they are fixed in the arterial walls. The method which is utilized for deploying the graft is relatively simple and can be accomplished within a relatively short period of time.--.

Signed and Sealed this

Eleventh Day of April, 2000

Attest:

Q. TODD DICKINSON

*Attesting Officer*        *Director of Patents and Trademarks*